United States Patent [19]

Cohen et al.

[11] 4,317,035

[45] Feb. 23, 1982

[54] GOLD MONITORING PROCEDURE

[75] Inventors: Richard L. Cohen, Berkeley Heights, N.J.; Ronald L. Meek, Lee's Summit, Mo.

[73] Assignees: Western Electric, New York, N.Y.; Bell Telephone Laboratories, Incorporated, Murray Hill, N.J.

[21] Appl. No.: 105,619

[22] Filed: Dec. 20, 1979

[51] Int. Cl.³ ............................................. G01N 23/20
[52] U.S. Cl. .................................... 250/272; 250/273
[58] Field of Search ........... 250/252, 272, 273, 277 R, 250/358 R, 359, 460

[56] References Cited

U.S. PATENT DOCUMENTS

| | | | |
|---|---|---|---|
| 3,433,954 | 3/1969 | Bowman et al. | 250/272 |
| 3,984,679 | 10/1976 | Lublin et al. | 250/272 |
| 4,152,591 | 5/1979 | Averitt et al. | 250/272 |

*Primary Examiner*—Alfred E. Smith
*Attorney, Agent, or Firm*—Walter G. Nilsen

[57] ABSTRACT

A gold plating process is described in which gold concentration is monitored by a radioactive excitation procedure. This procedure for measuring gold concentration requires no chemical manipulation and yields immediate results. The procedure can be adapted to continuous concentration measurement for use in automatic control of gold concentration in a gold plating procedure.

11 Claims, 4 Drawing Figures

GOLD MONITORING PROCEDURE

TECHNICAL FIELD

The invention relates to a process for plating gold.

BACKGROUND OF THE INVENTION

Gold plating processes have many important industrial applications including the production of jewelry, optical devices, as well as the fabrication of electronic circuits and components.

In recent years, the use of gold in such industrial applications has been increasing very rapidly. At the same time, the cost of gold has been rising dramatically. For these reasons, it is economically advantageous to devise ways of saving gold, as well as ways of making gold plating processes more efficient. In particular, it is highly advantageous to be able to measure and control gold concentration in a convenient way.

There are several advantages to the use of gold as a surface metallic film. First of all, it does not form a surface insulating film such as an oxide film. This insures that gold has and retains a high surface luster which is quite attractive when used in jewelry articles. For the same reason, the optical reflectivity properties of gold are quite attractive which makes its use in optical devices highly desirable. Again, because no surface insulating film is formed, the use of gold in electric circuits and components is highly desirable. In particular, its use in electrical contact devices such as relays, contacts and electrical connectors is highly advantageous because surface contact to gold has low electrical resistance.

Gold also has the advantage of being chemically inert. This chemical property is responsible for the fact that no insulating or oxide layer is formed on the gold surfaces. Because of this chemical property, the use of gold insures long device lifetime and high device reliability since gold is not affected by most chemicals or adverse conditions of temperature and humidity. This is particularly advantageous in the production of integrated circuits where relatively thin conducting paths are often used. Here, stability and chemical inertness are unusually important so that the properties of these conducting paths are not changed with time. Many metals (for example, copper) might have satisfactory electrical properties for these applications, but they rapidly degrade with time, and alter their conductive properties. In addition to the inert chemical properties of gold, it also has the advantage of exhibiting high electrical conductivity.

Because of its high electrical conductivity, and chemical inertness, gold is often used as an electrical contact metal in electrical connectors, switches and relays. By the addition of small amounts of various elements (for example, arsenic, cobalt, nickel, etc.), gold can be made quite hard and resistant to abrasion. Thus, gold makes an excellent electrical contact metal for connectors and relays and is extensively used in this application.

It is highly advantageous economically to be able to produce reliable electrical contacts very rapidly and at low cost. In particular, rapid gold plating procedures are highly desirable. In order to insure gold plating quality, it is desirable to be able to monitor gold plating efficiency. This requires a method of measuring gold concentration very rapidly and in such a way that the results are immediately available. Most procedures for determining gold concentration either are very slow and yield results only after extensive chemical manipulations, or are unduly sensitive to the type and concentration of the supporting electrolyte used in the plating bath, or depend on the chemical state of the gold. In some gold plating procedures, it is advantageous to have a continuous monitoring procedure which indicates gold concentration in the plating bath.

SUMMARY OF THE INVENTION

The invention is a process for plating gold in which the concentration of gold in the gold plating solution is monitored by an X-ray fluorescence procedure. The procedure involves excitation of the gold with high energy radiation and measurement of the X-ray fluorescence given off. The excitation should involve sufficiently high energy photons so as to insure sufficient X-ray fluorescence for measurement. Much background material on X-ray fluorescence measurements is given in a book entitled, *Principles of Practice of X-Ray Spectrometric Analysis* by Eugene P. Bertin, Plenum Press, New York, 1975, Second Edition. The advantage of this type of gold plating process is that gold concentration measurements do not involve any chemical manipulation or use of chemical reagents. The concentration measurement has wide applicability since the measurement does not depend on the chemical state of gold. Also, the gold plating solution is not affected and measurements can be made directly on the gold plating bath in situ or using a flow-through cell. Since results are immediately available, they can be used in an automatic control procedure so as to insure optimum plating conditions. Inexpensive plastic vials (such as polyethylene vials) can be used and exact alignment is not required. Indeed, a particularly significant advantage of the procedure is that highly reproducible results can be obtained using unskilled personnel. The monitoring procedure is applicable to a variety of gold plating processes including electroplating, displacement plating, electroless plating and autocatalytic plating. Typical gold plating processes are described in various publications including, F. H. Reid, et al, *Gold Plating Technology* (1974); F. H. Lowenheim, *Modern Electroplating*, Third Edition, 1974; and W. S. Rapson, et al, *Gold Usage*, Academic Press, New York 1978.

DETAILED DESCRIPTION

Figure 1:
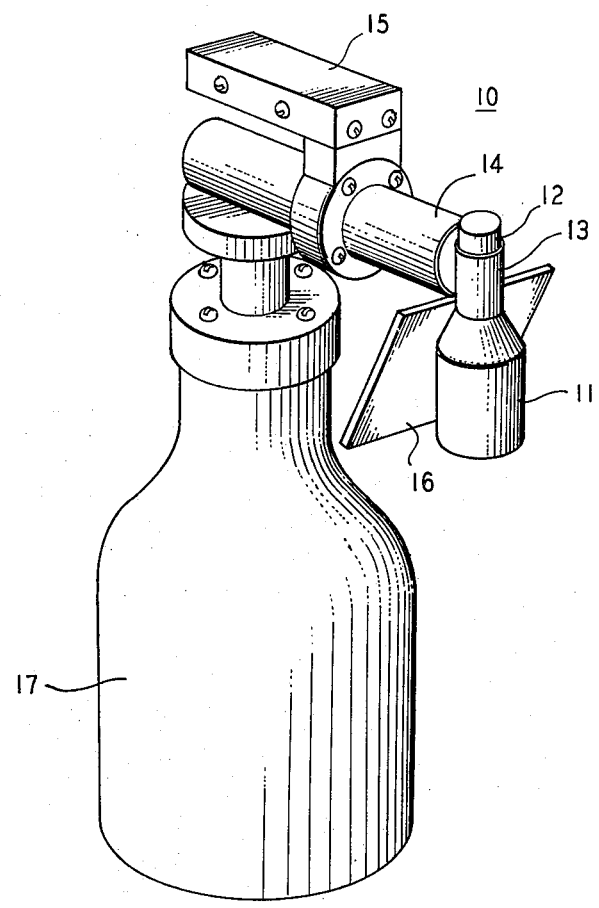
FIG. 1 shows a block diagram of an apparatus used to measure gold concentration by X-ray fluorescence.

The procedure for determining gold concentration is based on an X-ray fluorescence procedure. In this procedure, the gold species (atomic or ionic species) are excited by a radiation source and the resulting X-ray fluorescence characteristic of gold detected by a variety of procedures. The efficiency of the gold detecting procedure depends strongly on the intensity and energy of the excitation source.

The exciting photon energies may vary over fairly large ranges, provided they are above the excitation energy necessary to excite the particular X-ray fluorescence being detected. For example, in the case of gold, excitation energies of at least 3.4 keV are required for M level X-ray fluorescence, 14.4 keV for L level X-ray fluorescence and 81 keV for K level X-ray fluorescence.

Best results are obtained where the excitation photon energies are just above the K level excitation energies for gold (81 keV). This type of excitation yields strong X-ray fluorescence in the 69 keV region.

A particular advantage of using excitation radiation in this region is that the aqueous solution and supporting electrolyte of the gold plating bath produce very little background X-ray fluorescence radiation. Strong background radiation would reduce the accuracy of the measurement and require large corrections to the measurements. With reduced background radiation, measurements can be used directly to determine gold concentrations or in an automatic concentration control apparatus. In addition, the fluorescent X-rays given off at 69 keV have relatively small cross-sections to be absorbed or scattered by water and other species used in the plating solution and for hydrocarbon plastics. Thus, from the standpoint of specificity, sensitivity and minimization of errors from geometric variations, radiation in this energy range is preferred.

A variety of sources of ionizing radiation may be used provided they emit radiation of sufficiently high energy to excite X-ray fluorescence from the desired transition of the gold species. Particularly convenient excitation sources are radioactive species that give off radiation of sufficiently high energy to excite the desired X-ray fluorescence. Although a variety of radioactive sources may be used, two sources are particularly convenient from the standpoint of long half life (so that the intensity of the excitation energy remains relatively constant), energy of the exciting radiation, and availability. These two sources are $Co^{57}$ and $Eu^{155}$. The cobalt source has strong emission in the 122 keV gamma ray region, and is readily available. It has a half life of 271 days so that for accurate work, a correction for decreased excitation intensity is needed.

The radioactive source $Eu^{155}$ has certain advantages over $Co^{57}$. It has a longer half life (5 years) so that corrections for decreased excitation intensity are much smaller and often negligible. Also, the source need not be replaced as often.

The $Eu^{155}$ radioactive source gives off gamma rays in the 86 and 105 keV region. These energy regions are much more efficient for exciting K shell X-ray fluorescence than the 122 keV gamma radiation of $Co^{57}$. Although $Co^{57}$ is more readily available than $Eu^{155}$, the latter radioactive source can easily be made by neutron irradiation.

After simple excitation, the resulting X-ray fluorescent is sampled by the detector. It is preferred that the geometry be such as to minimize extraneous scattering from the sample. Both energy selection and detection are needed in the measurement. Energy selection is required so as to select, as far as possible, X-ray fluorescence from gold species. Such energy selection may be done before or after detection. A typical set up is to use a diffracting crystal monochromator followed by a detector such as a geiger counter.

In recent years, solid state "non-dispersive" semiconducting detectors of very high efficiencies have found use in detecting and analyzing (as to energy spectrum) X-rays. The entire (energy) spectrum of X-rays is detected and energy selection is made by means of a pulse height selection system. A germanium solid state detector is preferred at the present time, because of greater sensitivity for the high energy X-rays. For greater resolution, the detector is cooled, typically to liquid nitrogen temperatures.

In a typical apparatus, signals from the detector are fed into a pre-amplifier (often made part of the detector system) and then into a standard pulse shaping amplifier. The output of the amplifier is in the form of pulses which correspond to the energy of the fluorescent X-rays. A pulse height selector is used to select the pulses that correspond to the particular energy X-rays which correspond to the K level fluorescence of gold. A particular advantage of using high energy excitation and the K level fluorescence of the gold is that scattering in the sample in this energy region is very much smaller than at lower energies. The output of the pulse height selector is fed into a conventional counter. In typical experiments, detector resolution was approximately 1 keV so that both $AuK_{\alpha 1}$ and $AuK_{\alpha 2}$ lines are accepted into a single channel. This maximizes the counting rate without serious degradation in selectively.

FIG. 1 shows a typical apparatus for carrying out gold concentration measurements by the X-ray fluorescence method. The excitation source (typically 3 millicuries of $Co^{57}$) is located in a brass-lined lead collimator 11. The collimator also serves as a shield against escape of radiation from the excitation source. This excitation source emits gamma rays (mainly in the 122 keV region) which pass through the sample vial 12 located inside the sample vial holder 13. Sample holder design is of importance to insure that errors in measurement do not occur due to variation in the positioning of the sample. The lead in the collimator 11 prevents gamma rays from escaping the collimator. A portion of the X-ray fluorescence produced in the sample falls on the detector housing 14 which contains both cooled germanium detector and pre-amplifier 15. Also shown in FIG. 1 is a copper shield 16 which reduces errors due to radiation from the collimator reaching the detector housing. Also shown is a liquid nitrogen container 17 which is used to cool the germanium detector.

Figure 2:
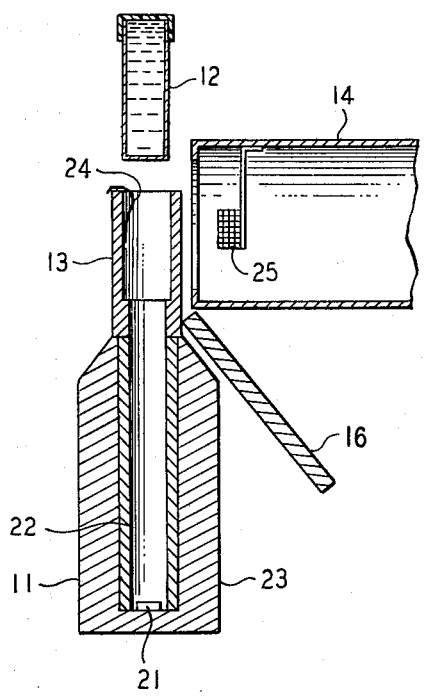
FIG. 2 shows a cross-section of the lead collimator, sample holder and detector.

FIG. 2 shows a cross-sectional view of part of the apparatus shown in FIG. 1. This cross-sectional view shows the geometry of the apparatus somewhat more clearly than the drawing in FIG. 1. The radioactive source 21 is located at the bottom of the collimator 11 with inside liner 22 made of brass and outside 23 made of lead. Radiation from the source 21 travels up the collimator toward the sample holder 13 with mylar spring 24 which holds the sample vial 12 in place. This spring and holder design insures reproducible sample location which minimizes geometrical errors. Also shown is a germanium solid state detector 25 in a detector housing 14. A copper shield 16 is located between collimator 11 and detector housing to reduce radiation originating from the source from reaching the detector.

Figure 3:
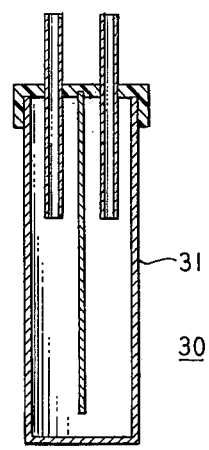
FIG. 3 shows a side view of a particular type of flow-through sample vial.

FIG. 3 shows a sample vial 12 useful in continuous flow measurements. It is designed so that the sample vial remains in place and plating solution continuously pumped through the vial.

Figure 4:
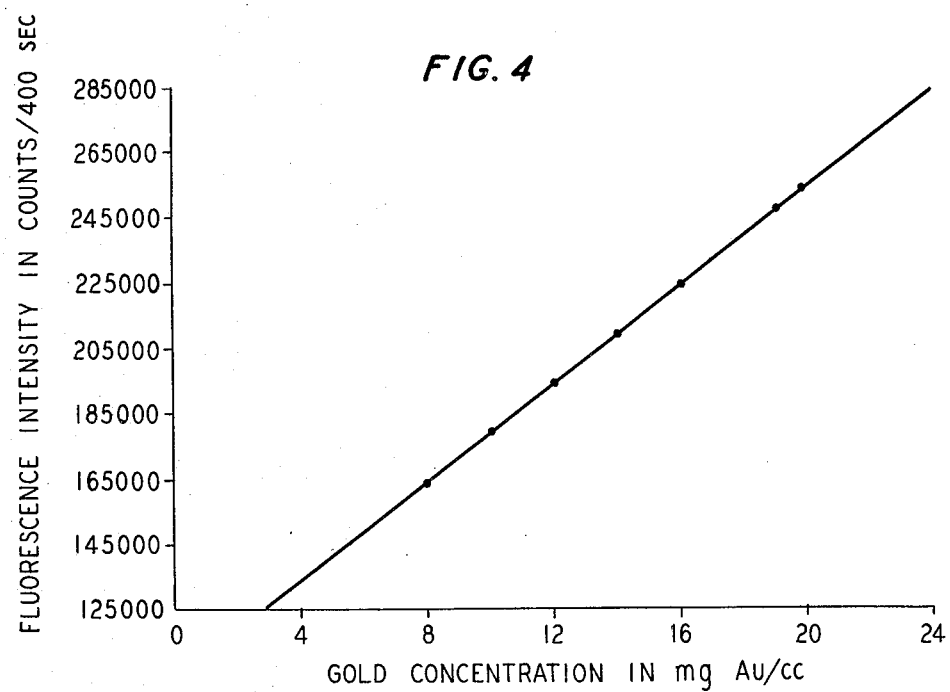
FIG. 4 shows a calibration curve in which counts from a radiation detector are plotted against gold concentration of a gold plating bath sample.

In order to illustrate the method described here, a calibration curve was made using solutions with known gold concentrations. The counting time was 400 seconds for each point. This yielded sufficient counts so that the intrinsic statistical variations for a random process is sufficiently low to give results of the required accuracy. The results are set forth in FIG. 4 in the form of a calibration curve.

Two things are worthy of note in the calibration curve. First, a reasonable number of counts are obtained in the gold concentration range of interest in gold plating. Second, the calibration is nearly a straight line so that a linear relationship between count rate and gold concentration should be adequate for most applications. Also, the near proportionally between count rate and gold concentration shows that the intensity of the X-ray fluorescence in the energy range around the Au$k_\alpha$ line is predominantly due to gold and not water or other substance around the gold sample. This conclusion was also checked by direct experiment. Measurements on samples with known gold concentration show accuracies in the one percent range.

What is claimed is:

1. A process for plating gold from a gold plating solution including the step of measuring gold concentration in the gold plating solution characterized in that the gold concentration is measured by exposing the gold plating solution to radiation from a radioactive source emitting photons of sufficiently high energy to excite X-ray fluorescence from the gold and detecting the resulting X-ray fluorescence with a solid state detector.

2. The process of claim 1 in which the radioactive source is selected from the group consisting of $Co^{57}$ and $Eu^{155}$.

3. The process of claim 1 in which the excitation energy from the radioactive source is greater than 81 keV.

4. The process of claim 1 in which the solid state detector is a germanium detector.

5. The process of claim 4 in which the germanium detector is cooled below room temperature.

6. The process of claim 5 in which the germanium detector is cooled to liquid nitrogen temperatures.

7. The process of claim 1 in which the energy band of the X-ray fluorescence for gold is selected by means of pulse height selection of the output of the solid state detector.

8. The process of claim 7 in which the fluorescence lines selected are the K lines.

9. The process of claim 1 in which a plastic sample vial is used.

10. The process of claim 9 in which the sample vial is made of polyethylene.

11. The process of claim 1 in which the measurement of gold concentration is made on a continuously flowing solution.

* * * * *